United States Patent
Ritzmann et al.

(10) Patent No.: US 10,690,642 B2
(45) Date of Patent: Jun. 23, 2020

(54) METHOD FOR AUTOMATICALLY GENERATING A FLUID PROPERTY LOG DERIVED FROM DRILLING FLUID GAS DATA

(71) Applicants: Nicklas Ritzmann, Celle (DE); Oliver Mohnke, Celle (DE); Holger Frank Thern, Hannover (DE)

(72) Inventors: Nicklas Ritzmann, Celle (DE); Oliver Mohnke, Celle (DE); Holger Frank Thern, Hannover (DE)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 214 days.

(21) Appl. No.: 15/277,547

(22) Filed: Sep. 27, 2016

(65) Prior Publication Data
US 2018/0088096 A1    Mar. 29, 2018

(51) Int. Cl.
*G01N 33/00* (2006.01)
*E21B 49/08* (2006.01)
(Continued)

(52) U.S. Cl.
CPC ....... *G01N 33/0036* (2013.01); *E21B 49/084* (2013.01); *G01N 24/081* (2013.01);
(Continued)

(58) Field of Classification Search
CPC  G01N 33/0036; G01N 24/082; E21B 49/084; E21B 10/00; E21B 2049/085
See application file for complete search history.

(56) References Cited

U.S. PATENT DOCUMENTS 4,578,579 A * 3/1986 Dion ............... G01V 11/00
                                                    250/253
4,765,182 A * 8/1988 Boone ............. E21B 49/005
                                                    175/50
(Continued)

FOREIGN PATENT DOCUMENTS

WO    2012052962 A1    4/2012
WO    2015050025 A1    4/2015
(Continued)

OTHER PUBLICATIONS

Abu-Shanab, et al.; "Improved Porosity Estimation in Tight Gas Reservoirs from NMR and Density Logs"; (2005); Emirates Journal for Engineering Researc, 10 (2); 5 pages.
(Continued)

*Primary Examiner* — Mohammad K Islam
(74) *Attorney, Agent, or Firm* — Cantor Colburn LLP

(57) ABSTRACT

A method for generating a log of a value of a property of a fluid in an earth formation versus depth includes: obtaining a plurality of samples of drilling fluid that are entrained with a formation gas and correlating each sample to a depth in a borehole from which the formation gas was entrained in the drilling fluid; extracting the formation gas from each sample to provide a plurality of gas samples; analyzing each formation gas sample to provide a chemical composition of each formation gas sample in the plurality of formation gas samples; and determining a property value of the fluid in the earth formation versus depth using the chemical composition of each formation gas sample in the plurality of formation gas samples to provide the log.

18 Claims, 2 Drawing Sheets

(51) Int. Cl.
*E21B 10/00* (2006.01)
*G01R 33/44* (2006.01)
*G01N 24/08* (2006.01)

(52) U.S. Cl.
CPC ...... *G01R 33/448* (2013.01); *E21B 2049/085* (2013.01); *G01N 24/082* (2013.01)

(56) References Cited

U.S. PATENT DOCUMENTS

| | | | |
|---|---|---|---|
| 4,961,343 A * | 10/1990 | Boone | E21B 49/005 175/50 |
| 6,229,308 B1 | 5/2001 | Freedman | |
| 6,331,775 B1 | 12/2001 | Thern et al. | |
| 6,737,864 B2 | 5/2004 | Prammer et al. | |
| 7,053,611 B2 | 5/2006 | Freedman | |
| 7,176,682 B2 | 2/2007 | Galford et al. | |
| 7,298,142 B2 | 11/2007 | Hursan et al. | |
| 7,511,487 B2 | 3/2009 | Badry et al. | |
| 7,538,547 B2 | 5/2009 | Heaton | |
| 7,623,968 B2 | 11/2009 | Griffiths et al. | |
| 8,165,817 B2 | 4/2012 | Betancourt et al. | |
| 8,558,165 B2 | 10/2013 | Evans et al. | |
| 8,614,573 B2 | 12/2013 | Minh | |
| 8,736,263 B2 | 5/2014 | Minh | |
| 8,838,390 B1 * | 9/2014 | Selman | E21B 44/00 166/264 |
| 8,965,703 B2 | 2/2015 | Prakash et al. | |
| 9,285,497 B2 | 3/2016 | Chen et al. | |
| 2004/0174166 A1 * | 9/2004 | Wisler | G01R 33/383 324/303 |
| 2006/0032301 A1 * | 2/2006 | DiFoggio | E21B 49/081 73/152.18 |
| 2008/0147326 A1 * | 6/2008 | Ellis | G01V 9/007 702/9 |
| 2008/0156327 A1 * | 7/2008 | Hollis | B63C 11/02 128/204.21 |
| 2009/0050369 A1 * | 2/2009 | Pop | E21B 49/005 175/42 |
| 2009/0193889 A1 * | 8/2009 | Waid | E21B 49/08 73/32 A |
| 2009/0288881 A1 * | 11/2009 | Mullins | E21B 7/04 175/50 |
| 2010/0088033 A1 * | 4/2010 | Chen | G01N 24/081 702/8 |
| 2010/0223989 A1 | 9/2010 | Reid et al. | |
| 2011/0061439 A1 | 3/2011 | Dong et al. | |
| 2011/0100710 A1 * | 5/2011 | Fossli | E21B 7/12 175/7 |
| 2011/0266056 A1 * | 11/2011 | Pop | E21B 49/08 175/50 |
| 2013/0085675 A1 * | 4/2013 | Prakash | E21B 49/003 702/9 |
| 2013/0295677 A1 | 11/2013 | Jones et al. | |
| 2013/0311096 A1 * | 11/2013 | Greer | G01N 30/88 702/9 |
| 2014/0214325 A1 * | 7/2014 | Wessling | E21B 47/06 702/11 |
| 2014/0253116 A1 * | 9/2014 | Freedman | G01R 33/30 324/303 |
| 2014/0300895 A1 * | 10/2014 | Pope | E21B 47/102 356/301 |
| 2014/0320126 A1 | 10/2014 | Heaton et al. | |
| 2015/0219782 A1 | 8/2015 | Kadayam Viswanatha et al. | |
| 2016/0102510 A1 * | 4/2016 | Mitchell | E21B 47/102 175/24 |
| 2016/0238739 A1 | 8/2016 | Cao Minh et al. | |
| 2018/0087368 A1 * | 3/2018 | Mills | E21B 43/38 |

FOREIGN PATENT DOCUMENTS

| | | |
|---|---|---|
| WO | 2015051133 A1 | 4/2015 |
| WO | 2015156811 A1 | 10/2015 |

OTHER PUBLICATIONS

Freedman, et al.; "Fluid Chracterization Using Nuclear Magnetic Resonance Logging"; (May-Jun. 2004); Petrophysics, vol. 45, No. 3; 10 pages.

Hamada, et al.; "Nuclear Magnetic Resonance Log Evaluation of Low Resistivity Sandstone Reservoirs By-Passed By Conventional Logging Analysis"; (2000); Retrieved from the Internet, http://www.ux.uis.no/~s-skj/ipt/Proceedings/SCA. 1987-2004/1-SCA2000-50.pdf; 6 pages.

Hamada, et al; "Better Porosity Estimate of Gas Sandstone Reservoirs Using Density and NMR Logging Data"; (2008); Emirates Journal for Engineering Research, 13 (3); 8 pages.

Hirasaki, et al. "NMR Properties of Reservoir Fluids";(2002); Retrieved from the internet http://porousmedia.rice.edu/resources/AAPG_Fluid2.pdf; 54 pages.

Reda, et al.; Precise Method Using Resistivity Imaging Tool for Estimation of High Resolutioin Reservoir Parameters Calibrated to Reservoir Description Tool and Nuclear Magnetic Resonance Data for Better Reservoir Characterization; SPE 126331; 2010; Society of Petroleum Engineers; 35 pages.

Reppert; et al.; Porosity and Water Saturation From LWD NMR in a North Sea Chalk Formation; 2005; SPWLA 46th Annual Logging Symposium, Jun. 26-29; 12 pages.

Van Steene, et al.; "Fluid Identification in Light Hydrocarbons Using NMR and Downhole Fluid Analyzers"; SPE 150886; 2012; Society of Petroleum Engineers; 13 pages.

International Search Report and the Written Opinion of the International Searching Authority, or the Declaration: PCT/US2017/053385; dated Jan. 4, 2018; 12 pages.

* cited by examiner

US 10,690,642 B2

METHOD FOR AUTOMATICALLY GENERATING A FLUID PROPERTY LOG DERIVED FROM DRILLING FLUID GAS DATA

BACKGROUND

Earth formations may be used for various purposes such as hydrocarbon production, geothermal production and carbon dioxide sequestration. In order to efficiently use resources, such as drilling or production resources, related to the utilization of the earth formations, it is important for petro-analysts or engineers to acquire detailed information about the formations. Hence, it would be appreciated in the drilling and production industries if improvements to the characterization of earth formations were provided.

BRIEF SUMMARY

Disclosed is a method for generating a log of a value of a property of a fluid in an earth formation versus depth. The method includes: obtaining a plurality of samples of drilling fluid that are entrained with a formation gas and correlating each sample to a depth in a borehole from which the formation gas was entrained in the drilling fluid; extracting the formation gas from each sample to provide a plurality of gas samples; analyzing each formation gas sample to provide a chemical composition of each formation gas sample in the plurality of formation gas samples; and determining a property value of the fluid in the earth formation versus depth using the chemical composition of each formation gas sample in the plurality of formation gas samples to provide the log.

Also disclosed is an apparatus for generating a log of a value of a property of a fluid in an earth formation versus depth. The apparatus includes: a drilling fluid sampler configured to obtain a plurality of samples of drilling fluid that are entrained with a formation gas, each sample being correlated to a depth in a borehole from which the formation gas was entrained in the drilling fluid; a gas extractor configured to extract the formation gas from each sample of drilling fluid in the plurality of samples of drilling fluid to provide a plurality of formation gas samples; a gas analyzer configured to analyze each formation gas sample in the plurality of formation gas samples to provide a chemical composition of each of the formation gas samples in the plurality of formation gas samples; and a processor configured to determine a property value of the fluid in the earth formation using the chemical property of each formation gas sample in the plurality of formation gas samples and to associate each determined property value with the depth in the borehole from which formation gas in each sample of drilling fluid was entrained in the drilling fluid to provide the log.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method presented herein by way of exemplification and not limitation with reference to the figures.

Disclosed are embodiments of methods and apparatuses for generating a log of one or more properties of formation fluid versus depth for a selected depth interval. In one or more embodiments, property values may be presented every few inches to provide a nearly continuous formation fluid property log. To obtain the formation fluid property log, samples of drilling fluid that have passed through a borehole penetrating the formation are obtained at the surface while a borehole is being drilled. The cutting or disintegrating of formation rock for drilling the borehole causes formation gas to be entrained in the drilling fluid, generally at the depth where a drill bit interacts with the formation rock. By knowing the geometries of the borehole and drill string and the flow rate of the drilling fluid, each sample can be correlated with the depth from which the gas was entrained in the sample. The sample is processed to release the gas entrained in the drilling fluid. The gas is then analyzed by an analyzer to determine the chemical composition of the gas. Using known equations or correlations, one or more properties of the formation fluid can be determined for each sample and, thus, for each sampled depth. The one or more properties can then be presented as a log. The log can then be used for performing further actions or analysis.

Figure 1:
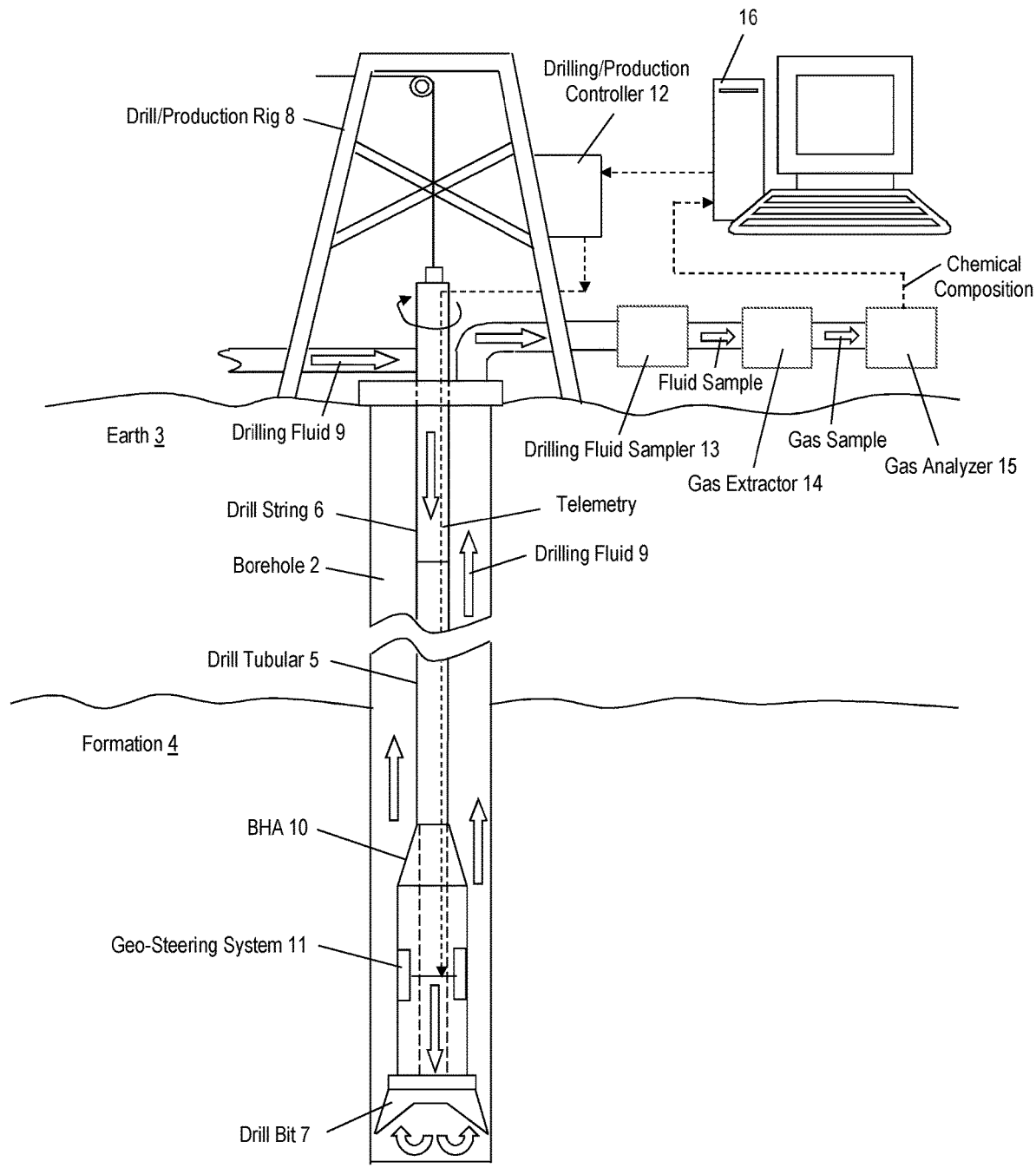
FIG. 1 is a cross-sectional view of an embodiment of a drill string disposed in a borehole penetrating the earth.

FIG. 1 is a cross-sectional view of an embodiment of a drill tubular 5 disposed in a borehole 2 (may also be referred to as a wellbore) penetrating the earth 3. The earth 3 includes a formation 4 that may have a formation fluid. The drill tubular 5 may be a drill string 6 or coiled tubing as known in the art. Coupled to the distal end of the drill tubular 5 is a drill bit 7 configured to cut or disintegrate formation rock to drill the borehole 2. A drill/production rig 8 is configured to rotate the drill string 6 and thus rotate the drill bit 7 in order to drill the borehole 2. The drill/production rig 8 is also configured to pump drilling fluid 9 through the interior of the drill tubular 5 in order to lubricate the drill bit 7 and flush cuttings from the borehole 2. The drill/production rig 8 may further be configured to perform production actions such as hydraulically fracturing the formation 4 at a selected depth interval or perforating a casing lining the borehole 2 at a selected depth as non-limiting examples. A geo-steering system 11 may be used to steer the drill bit 7 in accordance with a desired borehole trajectory, which may be selected based upon the formation fluid property log. The geo-steering system 11 and the drill bit 7 may be part of a bottomhole assembly (BHA) 10. The BHA 10 may include a mud motor (not shown) for turning the drill bit 7. The drill/production rig 8 may include a controller 12 that is configured to control drilling and/or production operations.

Disposed at the surface of the earth 3 is a drilling fluid sampler 13 configured to obtain a sample of the drilling fluid that flows to the surface of the earth through the borehole 2. The drilling fluid sampler 13 may include a pump (not shown) such as a displacement pump for obtaining a sample having a known volume. The sample may then be disposed in a gas extractor 14 configured to extract gas in the sample to provide a gas sample. The gas extractor 14 may include an agitator (not shown) that agitates the drilling fluid sample to cause the sample to release the gas and have the gas float to the surface of the sample. The gas extractor 14 may further include a gas vacuum (not shown) configured to suction the released gas to provide the gas sample. The gas sample may then be disposed in a gas analyzer 15 configured to determine the chemical composition of the gas sample. Non-limiting embodiments of the gas analyzer 15 include a gas chromatograph, an infrared spectrometer, and a mass spectrometer. The chemical composition of each gas sample may be entered into a computer processing system 16.

The samples of drilling fluid may be obtained at specified depth intervals, which can be close together enough to provide a nearly continuous spectrum of samples. In one or more embodiments, depth-resolution of the samples may be sub-feet such as where the samples are obtained every six inches. Other depth intervals may be selected depending on the spatial variation of the properties of the formation of interest. In one or more embodiments, the depth at which the drilling fluid for each sample is obtained may be determined by recording the time at which the sample is obtained at the surface. The travel time of the drilling fluid for the sample from the bottom of the borehole to the surface may be determined by dividing the depth of the borehole by the velocity of the drilling fluid traveling to the surface. The travel velocity may be determined by dividing the volume flow rate of the drilling fluid, as determined by a sensor or analysis, by the area of the annulus between the drill tubular 5 and the wall of the borehole 2. Thus, the time at which the drilling fluid of the sample passes the bottom of the borehole where the formation rock is being drilled is the time the sample is obtained at the surface minus the sample travel time. Accordingly, from a record of the depth of the borehole versus time, the depth at which the drilling fluid for the sample was obtained may be determined. The depth corresponding to each drilling fluid sample and thus each gas sample may also be entered into the computer processing system 16 to provide a log of formation gas composition versus depth.

Once the chemical composition of each gas sample is obtained, a property of the formation fluid at the depth corresponding to each gas sample may be determined from the chemical composition of the gas sample using a correlation known in the art. Non-limiting embodiments of the formation fluid property include density, T1 nuclear magnetic resonance (NMR) relaxation time, T2 NMR relaxation time, diffusion coefficient, hydrogen index, bubble point, API gravity or specific gravity, gas specific gravity, viscosity, and gas-oil-ratio. Once a formation fluid property of interest is determined using a known correlation, that formation property of interest may also be entered into the computer processing system 16, which can provide a log of the formation fluid property of interest versus depth. Alternatively, the computer processing system 16 may be configured to apply the known correlation to the chemical composition of each gas sample already entered. These known correlations combine the fluid composition with measured or anticipated formation properties, such as, but not limiting, pressure and temperature (e.g., PVT analysis) in order to derive the fluid characteristics such as, but not limiting, density, T1 nuclear magnetic resonance (NMR) relaxation time, T2 NMR relaxation time, diffusion coefficient, hydrogen index, bubble point, API gravity or specific gravity, gas specific gravity, viscosity, and/or gas-oil-ratio Thus, the computer processing system can be configured to associate the fluid property of interest with the corresponding depth at which the gas for the gas sample was obtained to provide the formation fluid property log versus depth.

Figure 2:
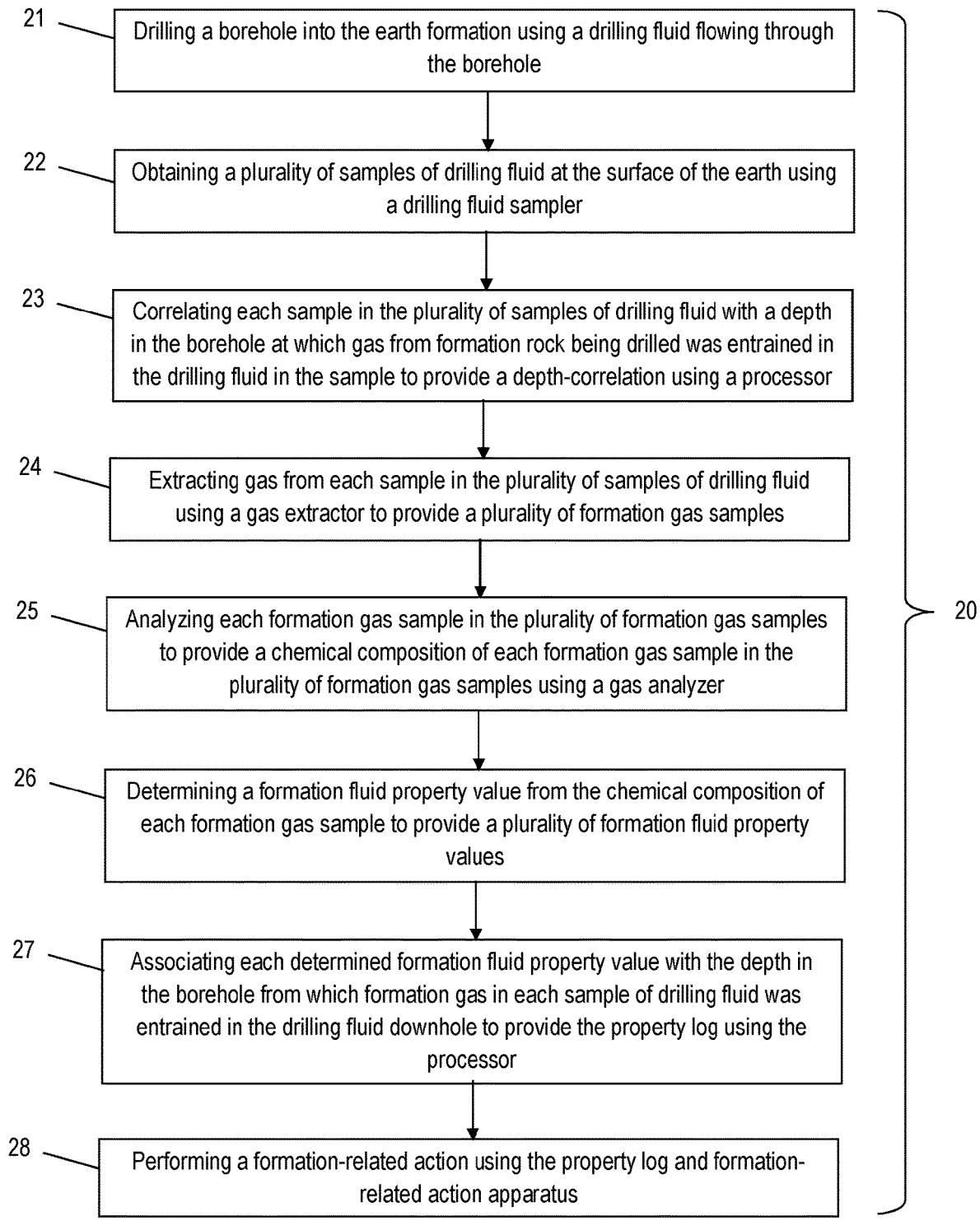
FIG. 2 is a flow chart for generating a log of a value of a property of a fluid in an earth formation versus depth.

FIG. 2 presents a flow chart for a method 20 for generating a property log of a fluid in an earth formation versus depth in the earth formation. Block 21 calls for drilling a borehole into the earth formation using a drilling fluid flowing through the borehole. In general, the drilling process causes entrainment of formation gas into the drilling fluid at the depth where the drilling is occurring. Block 22 calls for obtaining a plurality of samples of drilling fluid at the surface of the earth using a drilling fluid sampler. Block 23 calls for correlating each sample in the plurality of samples of drilling fluid with a depth in the borehole at which gas from formation rock being drilled was entrained in the drilling fluid in the sample to provide a depth-correlation using a processor. Block 24 calls for extracting gas from each sample in the plurality of samples of drilling fluid using a gas extractor to provide a plurality of formation gas samples. Block 25 calls for analyzing each formation gas sample in the plurality of formation gas samples to provide a chemical composition of each formation gas sample in the plurality of formation gas samples using a gas analyzer. Block 26 calls for determining a formation fluid property value from the chemical composition of each formation gas sample to provide a plurality of formation fluid property values. Block 27 calls for associating each determined formation fluid property value with the depth in the borehole from which formation gas in each sample of drilling fluid was entrained in the drilling fluid to provide the property log using the processor. The property log may be provided as an ordered set of property values and corresponding depth or as a printed or displayed graphical curve as non-limiting examples.

Block 28 calls for performing a formation-related action using the property log and formation-related action apparatus. In one or more embodiments, the formation-related apparatus is a drilling and/or production rig. In one or more embodiments, the formation-related action is drilling a borehole in accordance with a desired trajectory in order to efficiently access a reservoir of hydrocarbons in the earth formation. In one or more embodiments, the formation-related action is hydraulically fracturing the earth formation in a desired depth interval in order to extract hydrocarbons form that depth interval. In one or more embodiments, the formation-related action is perforating a casing lining the borehole at a desired depth.

It can be appreciated that by providing one or more formation property values as a function of depth with high resolution, such as on the order of inches, a mathematical formation model will have more accuracy than a conventional formation model that assumes one property value for all of the depths in the earth formation.

Set forth below are some embodiments of the foregoing disclosure:

Embodiment 1

A method for generating a log of a value of a property of a fluid in an earth formation versus depth, the method comprising: obtaining a plurality of samples of drilling fluid that are entrained with a formation gas and correlating each sample to a depth in borehole from which the formation gas was entrained in the drilling fluid; extracting the formation gas from each sample to provide a plurality of gas samples; analyzing each formation gas sample to provide a chemical composition of each formation gas sample in the plurality of formation gas samples; and determining a property value of the fluid in the earth formation versus depth using the chemical composition of each formation gas sample in the plurality of formation gas samples to provide the log.

Embodiment 2

The method according to any prior embodiment, further comprising drilling the borehole using a drill tubular through which the drilling fluid flows to where the earth formation is being drilled.

Embodiment 3

The method according to any prior embodiment, wherein the depth in a borehole from which the gas was entrained in the drilling fluid is a depth at which the borehole is being drilled by a drill bit coupled to the drill tubular.

Embodiment 4

The method according to any prior embodiment, further comprising obtaining the plurality of samples of drilling fluid at a surface of the earth by a drilling fluid sampler.

Embodiment 5

The method according to any prior embodiment, further comprising agitating each sample of drilling fluid to release formation gas.

Embodiment 6

The method according to any prior embodiment, further comprising operating a gas analyzer for analyzing each gas sample.

Embodiment 7

The method according to any prior embodiment, wherein the property comprises density, T1 nuclear magnetic resonance (NMR) relaxation time, T2 NMR relaxation time, diffusion coefficient, hydrogen index, bubble point, API gravity, gas specific gravity, viscosity, or gas-oil-ratio or any combination thereof.

Embodiment 8

The method according to any prior embodiment, further comprising operating formation-related apparatus for performing a formation-related action using the log.

Embodiment 9

The method according to any prior embodiment, wherein the formation-related action comprises at least one of drilling a borehole in accordance with a desired trajectory, hydraulically fracturing the earth formation in a desired depth range, and perforating a casing lining the borehole at a desired depth.

Embodiment 10

An apparatus for generating a log of a value of a property of a fluid in an earth formation versus depth, the apparatus comprising: a drilling fluid sampler configured to obtain a plurality of samples of drilling fluid that are entrained with a formation gas, each sample being correlated to a depth in a borehole from which the formation gas was entrained in the drilling fluid; a gas extractor configured to extract the formation gas from each sample of drilling fluid in the plurality of samples of drilling fluid to provide a plurality of formation gas samples; a gas analyzer configured to analyze each formation gas sample in the plurality of formation gas samples to provide a chemical composition of each of the formation gas samples in the plurality of formation gas samples; and a processor configured to determine a property value of the fluid in the earth formation using the chemical property of each formation gas sample in the plurality of formation gas samples and to associate each determined property value with the depth in the borehole from which formation gas in each sample of drilling fluid was entrained in the drilling fluid to provide the log.

Embodiment 11

The apparatus according to any prior embodiment, further comprising a drill tubular through which the drilling fluid flows to where the earth formation is being drilled by a drill bit.

Embodiment 12

The apparatus according to any prior embodiment, wherein the gas extractor is configured to agitate each sample of drilling fluid in order to release the formation gas.

Embodiment 13

The apparatus according to any prior embodiment, wherein the gas analyzer is at least one of a gas chromatograph, an infrared spectrometer, and a mass spectrometer.

Embodiment 14

The apparatus according to any prior embodiment, wherein the property comprises density, T1 nuclear magnetic resonance (NMR) relaxation time, T2 NMR relaxation time, diffusion coefficient, hydrogen index, bubble point, API gravity, gas specific gravity, viscosity, or gas-oil-ratio or any combination thereof.

Embodiment 15

The apparatus according to any prior embodiment, further comprising a formation-related apparatus configured to perform a formation-related action using the log.

Embodiment 16

The apparatus according to any prior embodiment, wherein the formation-related action comprises at least one of drilling a borehole in accordance with a desired trajectory, hydraulically fracturing the earth formation in a desired depth range, and perforating a casing lining the borehole at a desired depth.

In support of the teachings herein, various analysis components may be used, including a digital and/or an analog system. For example, the controller 12 and/or the computer processing system 16 may include digital and/or analog systems. The system may have components such as a processor, storage media, memory, input, output, communications link (wired, wireless, optical or other), user interfaces (e.g., a display or printer), software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a non-transitory computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a power supply (e.g., at least one of a generator, a remote supply and a battery), cooling component, heating component, magnet, electromagnet, sensor, electrode, transmitter, receiver, transceiver, antenna, controller, optical unit, electrical unit or electromechanical unit may be included in support of the various aspects discussed herein or in support of other functions beyond this disclosure.

Elements of the embodiments have been introduced with either the articles "a" or "an." The articles are intended to mean that there are one or more of the elements. The terms "including" and "having" and the like are intended to be inclusive such that there may be additional elements other than the elements listed. The conjunction "or" when used with a list of at least two terms is intended to mean any term or combination of terms. The term "configured" relates one or more structural limitations of a device that are required for the device to perform the function or operation for which the device is configured.

The flow diagram depicted herein is just an example. There may be many variations to this diagram or the steps (or operations) described therein without departing from the spirit of the invention. For instance, the steps may be performed in a differing order, or steps may be added, deleted or modified. All of these variations are considered a part of the claimed invention.

The disclosure illustratively disclosed herein may be practiced in the absence of any element which is not specifically disclosed herein.

While one or more embodiments have been shown and described, modifications and substitutions may be made thereto without departing from the spirit and scope of the invention. Accordingly, it is to be understood that the present invention has been described by way of illustrations and not limitation.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for generating a log of a value of a property of a fluid in an earth formation versus depth, the method comprising:
    obtaining a plurality of samples of drilling fluid that are entrained with a formation gas and correlating each sample to a depth in a borehole from which the formation gas was entrained in the drilling fluid;
    extracting the formation gas from each sample to provide a plurality of formation gas samples;
    analyzing each formation gas sample to provide a chemical composition of each formation gas sample in the plurality of formation gas samples;
    determining at least one formation property at the depth in the borehole from which the formation gas was entrained in the drilling fluid; and
    determining the value of the property of the fluid in the earth formation from the chemical composition of each formation gas sample in the plurality of formation gas samples and the at least one formation property at the depth in the borehole from which the formation gas was entrained in the drilling fluid to provide the value of the property of the fluid in the earth formation for each chemical composition at the depth in the borehole from which the formation gas in each sample of drilling fluid was entrained in the drilling fluid to provide the log using a processor.

2. The method according to claim 1, further comprising drilling the borehole using a drill tubular through which the drilling fluid flows to where the earth formation is being drilled.

3. The method according to claim 2, wherein the depth in a borehole from which the gas was entrained in the drilling fluid is a depth at which the borehole is being drilled by a drill bit coupled to the drill tubular.

4. The method according to claim 1, further comprising obtaining the plurality of samples of drilling fluid at a surface of the earth by a drilling fluid sampler.

5. The method according to claim 4, further comprising agitating each sample of drilling fluid to release formation gas.

6. The method according to claim 1, further comprising operating a gas analyzer for analyzing each gas sample.

7. The method according to claim 1, wherein the property of the fluid in the earth formation comprises density, T1 nuclear magnetic resonance (NMR) relaxation time, T2 NMR relaxation time, diffusion coefficient, hydrogen index, bubble point, API gravity, gas specific gravity, viscosity, or gas-oil-ratio or any combination thereof.

8. The method according to claim 1, further comprising operating formation-related apparatus for performing a formation-related action using the log.

9. The method according to claim 8, wherein the formation-related action comprises at least one of drilling a borehole in accordance with a desired trajectory, hydraulically fracturing the earth formation in a desired depth range, and perforating a casing lining the borehole at a desired depth.

10. An apparatus for generating a log of a value of a property of a fluid in an earth formation versus depth, the apparatus comprising:
    a drilling fluid sampler configured to obtain a plurality of samples of drilling fluid that are entrained with a formation gas, each sample being correlated to a depth in a borehole from which the formation gas was entrained in the drilling fluid;

a gas extractor configured to extract the formation gas from each sample of drilling fluid in the plurality of samples of drilling fluid to provide a plurality of formation gas samples;

a gas analyzer configured to analyze each formation gas sample in the plurality of formation gas samples to provide a chemical composition of each of the formation gas samples in the plurality of formation gas samples; and a processor configured to (i) receive at least one formation property at the depth in the borehole from which the formation gas was entrained in the drilling fluid and (ii) determine the value of the property of the fluid in the earth formation from the chemical composition of each formation gas sample in the plurality of formation gas samples and the at least one formation property at the depth in the borehole from which the formation gas was entrained in the drilling fluid to provide the value of the property of the fluid in the earth formation for each chemical composition at the depth in the borehole from which formation gas in each sample of drilling fluid was entrained in the drilling fluid to provide the log.

11. The apparatus according to claim 10, further comprising a drill tubular through which the drilling fluid flows to where the earth formation is being drilled by a drill bit.

12. The apparatus according to claim 10, wherein the gas extractor is configured to agitate each sample of drilling fluid in order to release the formation gas.

13. The apparatus according to claim 10, wherein the gas analyzer is at least one of a gas chromatograph, an infrared spectrometer, and a mass spectrometer.

14. The apparatus according to claim 10, wherein the property of the fluid in the earth formation comprises density, T1 nuclear magnetic resonance (NMR) relaxation time, T2 NMR relaxation time, diffusion coefficient, hydrogen index, bubble point, API gravity, gas specific gravity, viscosity, or gas-oil-ratio or any combination thereof.

15. The apparatus according to claim 10, further comprising a formation-related apparatus configured to perform a formation-related action using the log.

16. The apparatus according to claim 15, wherein the formation-related action comprises at least one of drilling a borehole in accordance with a desired trajectory, hydraulically fracturing the earth formation in a desired depth range, and perforating a casing lining the borehole at a desired depth.

17. The method according to claim 1, wherein the at least one formation property comprises at least one of pressure and temperature.

18. The apparatus according to claim 10, wherein the at least one formation property comprises at least one of pressure and temperature.

* * * * *